(12) United States Patent
Björnberg et al.

(10) Patent No.: US 7,576,256 B2
(45) Date of Patent: Aug. 18, 2009

(54) WOUND DRESSING WITH A BACTERIAL ADSORBING COMPOSITION

(75) Inventors: Sten G. Björnberg, Spånga (SE); Jan G. Smith, Askim (SE)

(73) Assignee: Abigo Medical AB, Askim (SE)

( * ) Notice: Subject to any disclaimer, the term of this patent is extended or adjusted under 35 U.S.C. 154(b) by 214 days.

(21) Appl. No.: 11/009,429

(22) Filed: Dec. 10, 2004

(65) Prior Publication Data

US 2006/0129080 A1    Jun. 15, 2006

(51) Int. Cl.
*A61F 13/00*    (2006.01)
(52) U.S. Cl. .............................. 602/48; 602/54; 602/56
(58) Field of Classification Search ................... 602/41, 602/48, 53–54, 56
See application file for complete search history.

(56) References Cited

U.S. PATENT DOCUMENTS

| | | | |
|---|---|---|---|
| 4,211,227 A | 7/1980 | Anderson et al. | |
| 4,275,721 A | 6/1981 | Olson | |
| 4,617,326 A * | 10/1986 | Bjornberg et al. | 428/536 |
| 4,643,180 A | 2/1987 | Feld et al. | |
| 4,643,181 A | 2/1987 | Brown | |
| 4,655,756 A | 4/1987 | Fawkes | |
| 4,678,704 A | 7/1987 | Fellows | |
| 4,832,009 A * | 5/1989 | Dillon | 602/58 |
| 5,098,417 A | 3/1992 | Yamazaki et al. | |
| 5,380,294 A | 1/1995 | Persson | |
| 5,447,492 A * | 9/1995 | Cartmell et al. | 602/58 |
| 5,498,416 A | 3/1996 | Carsenti-Etesse et al. | |
| 5,700,742 A | 12/1997 | Payne | |
| 5,707,736 A | 1/1998 | Levy et al. | |
| 5,817,325 A | 10/1998 | Sawan et al. | |
| 5,856,248 A | 1/1999 | Weinberg | |
| 5,941,840 A * | 8/1999 | Court et al. | 602/47 |
| 6,037,431 A * | 3/2000 | Shioji et al. | 526/320 |
| 6,160,196 A | 12/2000 | Knieler et al. | |
| 6,369,289 B1 | 4/2002 | Orr, III | |

* cited by examiner

*Primary Examiner*—Michael A. Brown
(74) *Attorney, Agent, or Firm*—Lynn E. Barber

(57) ABSTRACT

A wound dressing product, combining both a traditional dressing with a mounted absorbent material and a hydrophobic fabric attached thereto, which is to be placed towards the wound, and is capable of binding unwanted microorganisms. The wound dressing product protects the wound, absorbs exudate and reduces the number of pathogenic microorganisms, without using antimicrobial substances, and consists of three bonded layers: hydrophobic cellulose acetate fabric which binds microorganisms, an attached efficient absorbent material, and a backing (cover) which is preferably visually transparent, semi-permeable and self-adhesive.

16 Claims, 6 Drawing Sheets

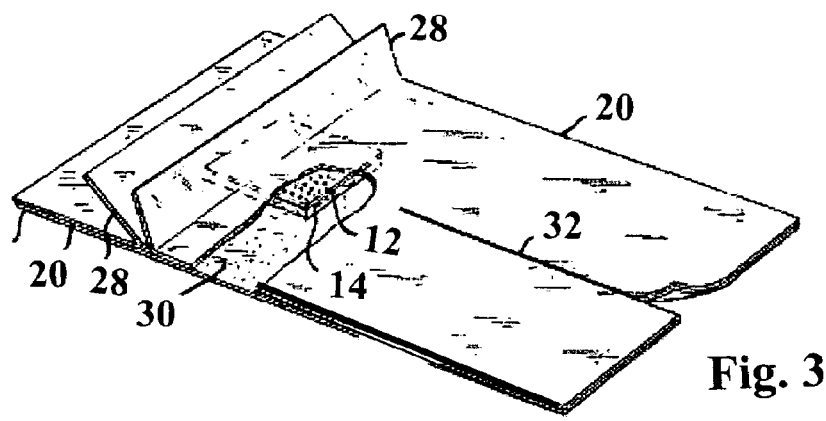
Fig. 3
Fig. 4
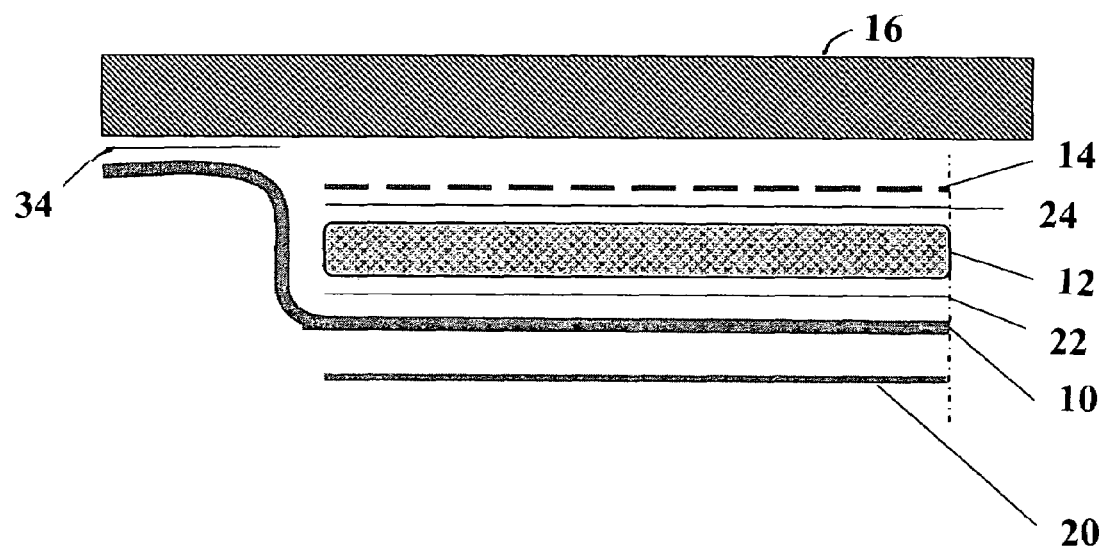

WOUND DRESSING WITH A BACTERIAL ADSORBING COMPOSITION

BACKGROUND OF THE INVENTION

1. Field of the Invention

The invention herein relates to a wound dressing product, combining both a traditional dressing including a mounted absorbent material on a film backing and a hydrophobic fabric attached thereto, facing towards the wound and being capable of binding unwanted micro organisms.

2. Description of the Related Art

The problem in healing of wounds associated with bacterial loads is for example tissue damage by release of toxins and enzymes, and possible spread of infections to the blood stream. Studies have shown that high tissue counts of microorganisms delay wound healing.

Numerous studies during the last few decades have also shown that bacteria, such as *Staphylococcus aureus* and Group A streptococci, both common wound pathogens, and the yeast *Candida albicans* commonly express profound cell surface hydrophobicity. Several structures which render the cell surface hydrophobic have been defined, like the fimbriae of *E. coli* which mediate adhesion to the intestinal wall, proteins on *C. albicans* which has been called "hydrophobins", and lipoteichoic acid in the cell wall of Gram-positive bacteria.

According to the hydrophobic principle of the laws of nature, a system will always struggle towards lowest possible energy consumption. When two water repellent molecules come into collision with each other they will increase the entropy and create disorder. The water molecules that surround the two hydrophobic molecules will force them together by hydrogen bonds between the water molecules although there is no force of attraction between the hydrophobic interaction, and will expel water molecules.

The initial step of infections of the skin and mucosal surfaces is microbial adhesion to wounded tissues. Several microbial components that adhesively bind to specific receptors have been identified, like fimbriae of Gram-negative enteric bacteria. Initial adhesion can be mediated by hydrophobic interactions between microbes and host tissue structures, and also by charge interactions. Binding of extra cellular matrix and serum proteins, like fibronectin, collagen and fibrinogen may further enhance colonization of deeper wound tissue.

In wound treatment, after tissue colonization wound microbes multiply, cause tissue damage by release of toxins and enzymes, and even spread to the blood stream. The human body has multiple defense mechanisms of the innate defense system. Also specific antibodies directed against the colonizing microorganism may be active to decrease the number of microorganisms. Numerous studies have shown that high tissue counts of microorganisms delay wound healing. On the other hand, small numbers of bacteria were shown to enhance the wound healing process in rodents by stimulating production of collagen-hydroxyproline.

Conventional treatment of wounds consists of mechanical cleansing with water, buffer solutions or disinfectants to remove bacteria and debris. This is of importance since debris hampers wound healing. The use of oxidizing agents (for example iodine tincture) or antiseptics (for example ointments comprising silver sulphadiazine) have been known for a long time. A number of disadvantages to these methods can be mentioned. For example, bacteria which have died remain in the wound, and wounds cannot be cleaned to remove the active compound reliably after the application, since it spreads in the entire wound. If these active compounds occur freely in the wound, they can also attack cells and substances in the wound fluid which promote wound healing.

Another method of wound treatment is the use of local antibiotics. Microbiologists disapprove of the use of local antibiotics since this is known to induce antibiotic resistance. Also in order to protect an already cleaned wound, including wounds from surgical cuts, various kinds of Band-Aid's, surgical tapes and dressings and the like have been used. Various kinds of cleaning and anti-microbial compounds added to such products been added or suggested for more long time effects.

What characterizes the related art in the field of the invention is that patented inventions are most often various fibrous materials and pads with added antimicrobial substances to be used with a separate bandage or fastened over wounds, using for example, surgical tape or various dressings. The invention for which patent protection is sought is a method of making an improved wound dressing product, combining both a traditional dressing with a mounted absorbent material plus a hydrophobic fabric which is capable of binding unwanted microorganisms and is attached to the absorbent material and placed towards the wound.

Products containing folded pads of bacteria-binding fabric and absorbing fabric, to be held together and on a wound by a separate bandage or tape, already exist in the market. However, not previously known are the products of the present invention in which an absorbent material is bonded to a hydrophobic material, such as a fiber, using a specially developed technique, allowing for transfer of liquids without separating the bond. In the invention herein this is combined with a backing (cover) which is visually transparent, semi-permeable and self-adhesive.

There are several known inventions relating to the use of antimicrobial substances and materials. One such example is the U.S. Pat. No. 6,369,289, which discloses the use of a cellulosic bandage in a method for covering an open wound by contacting the wound with the bandage having a calculated amount of antimicrobial agent. The disclosure of this patent and all other patents referred to herein is incorporate herein by reference. U.S. Pat. No. 4,655,756, relates to a non-woven material treated with a linear polymeric biguanide having a defined formula, or a mixture of, e.g., polyhexamethylene biguanide (PHMB).

Other types of antimicrobial agents are also known. For example, U.S. Pat. No. 5,707,736 discloses a dry, disposable, polymeric product having sustained-release antimicrobial activity that is formed from a polymeric material having an amine salt antimicrobial agent incorporated therein. The polymeric material may be in the form of fibers, sheets, films, and other stable woven, nonwoven and knitted materials. The antimicrobial agents include, e.g., chlorhexidine gluconate and chlorhexidine hydrochloride. Several similar uses of dressings combining antimicrobial compounds are known.

Other components of the invention, such as various kinds of adhesives, are also known as components of medical dressings. One such surgical dressing is described in U.S. Pat. No. 4,643,180, wherein the dressing comprises a sheet of polymeric film coated on one side with a water based adhesive of defined thickness which includes an antimicrobial agent deposited on the body-facing surface of the adhesive.

U.S. Pat. No. 4,643,181 also describes a surgical dressing and a process for making a surgical dressing. The dressing comprises a substrate coated on one surface with a solvent-based skin contact adhesive of defined thickness, the adhesive having distributed therein particles of antimicrobial substances.

U.S. Pat. No. 4,678,704 describes an impregnated fabric material comprising a fabric substrate to which has been applied an active cationic impregnant along with an anionic indicator dye in combination with a further cationic component, wherein the dye bonds to the further cationic component more readily than to the substrate and the further cationic component competes with the impregnant for bonding to the dye. The cationic impregnant may be a polymeric biguanide.

U.S. Pat. No. 5,098,417 relates to a wound dressing for systemic administration of a physiologically- or biologically-active agent by controlled release of the agent into such wound. The wound dressing comprises a substrate in the form of a fabric or cloth, at least a portion of which is cellulosic, which has been chemically modified to convert hydroxyl groups in the cellulosic portion to ionic-adsorbing sites, an ionic form of a physiologically- or biologically-active agent (which includes antibacterial agents) adsorbed in the substrate. The ionic bonds hold the agent temporarily to the substrate for controlled release therefrom in proportion to the amount of exudate in contact with the substrate and are formed by adsorbing the agent on the substrate at room temperature. The ionic bonds are disassociated upon contact with body exudate from wounds thereby to release the physiologically- or biologically-active agent in an amount in proportion to the amount of exudate in contact with the substrate.

U.S. Pat. No. 5,498,416 relates to a process for protection of prostheses, implants and/or catheters, and other temporary or permanent implantable materials against bacterial colonization and infection. An infection-resistant device is disclosed that is capable of progressively releasing in aqueous medium an amount of an antibacterial substance fixed to the device, the amount being effective to prevent bacterial contamination of the device. Devices are described to include urinary catheters, probes, vascular and intraarterial catheters, cardiacal valvular prostheses, arterial prostheses, cardiac simulators, orthopedic prostheses, ocular or dental implants, shunts that are connecting two segments of the circulatory system, and suture thread.

U.S. Pat. No. 5,700,742 relates to a method of treating a textile material to inhibit microbial growth, which comprises applying to the textile material an oligo or polymeric biguanide or salt thereof with an inorganic acid or an organic acid having a pK value above 4.5 followed by a strong organic acid having a pK value below 4.5 and free from any aliphatic or oxyalkylene chain containing 12 or more carbon atoms. A textile material treated in accordance with the claimed method is also disclosed.

U.S. Pat. No. 5,856,248 relates to cellulose fibers and products comprising cellulose fibers treated to absorb body secretions while substantially decreasing microbial growth, the fibers being chemically modified in a two-stage process comprising a first stage treatment with a water soluble salt of a transition metal and an alkali and a second stage treatment with a solution of a bisbiguanide compound, thereby forming a bond between the cellulose fibers, the transition metal and the compound. The process may utilize a rinsing step to neutral pH between the two aforementioned stages.

U.S. Pat. No. 5,817,325 relates to an article of manufacture having disposed on a surface thereof a contact-killing, non-leaching antimicrobial coating which kills microorganisms upon contact. The coating comprises an organic polycationic polymer matrix immobilized on the surface having bound or complexed thereto a surface-accessible antimicrobial metallic material such that the antimicrobial material does not release biocidal amounts of elutables into the surrounding environment.

Other patents relate to the so called SORBACT® products, which are folded dressing compositions including a hydrophobic fabric and a hydrophilic, liquid-absorbing material. U.S. Pat. No. 4,617,326 describes this principle. It has shown to be very difficult to adhere a strongly hydrophobic layer to hydrophilic liquid absorbent layers, and hence products made according to U.S. Pat. No. 4,617,326 have so far only been possible to manufacture by means of folding a separate layer in and around the hydrophilic absorbent layer and hydrophobic layer in order to keep the layers together. This is an important drawback, limiting the design and production of such wound pads.

Further, U.S. Pat. No. 6,160,196 relates to the same principle but adds thereto an antimicrobial active compound which is adapted to prevent infections from the outside of the pad, the antimicrobial compound is not be released into the wound. U.S. Pat. No. 4,211,227 discloses a non-woven surgical sponge material comprising a layered fabric having an inner core or a substantially hydrophilic material disposed adjacent at least one outer or surface layer, or between a pair of outer layers, of a substantially hydrophobic material. The sponge material is bonded by passing the material through rolls engraved in a pattern of lands and grooves such that a repeating pattern of three degrees of compression are imposed on the material. However, the so produced sponge is not using a hydrophobic material binding bacteria to any larger extent, nor does it have any backing which is visually transparent, semi-permeable and self-adhesive.

Further, there are several wound dressing products on the market containing absorbent pads, but without any anti microbial compounds or microbial binding materials, such products are Tegaderm® and Tegaderm® IV by 3M, (St. Paul, Minn. 55144-1000, U.S.A.) and OpSite Post-Op by Smith&Nephew (Memphis, Tenn. 38116, U.S.A.).

U.S. Pat. No. 5,380,294 discloses a vein catheter dressing with a supportive and adhesive foil combined with a liquid absorbing pad.

U.S. Pat. Nos. 4,275,721 and 5,380,294 describes vein catheter dressings with a centrally placed liquid absorbent pad located on an adhesive foil layer. The adhesive is covered with two separate release layers which is to be removed before application of the dressing. The dressings have a slit which departs from one end of the dressing to a short distance from the absorbent pad (U.S. Pat. No. 4,275,721), or up to or into the pad (U.S. Pat. No. 5,380,294).

U.S. Pat. No. 5,380,294 is distinguished from U.S. Pat. No. 4,275,721 by the addition of a transparent layer on and around the absorbent pad. The purpose of the transparent layer is to be able to inspect the incision place and the surrounding area in order to detect an eventual infection. The location of the transparent layer in U.S. Pat. No. 5,380,294 is limited to only the side of the pad opposite the slit.

Utilizing the Sorbact principle discussed above, products such as the Sorbact pad consist of folded acetate gauze and cotton gauze treated with the fatty acid ester DACC (dialkyl carbamoyl chloride). This provides Sorbact pads with a strong hydrophobic property. When the Sorbact pad gets in contact with pathogenic microorganisms in the wound surface, the microorganisms adhere to the pad through hydrophobic interaction. The method is based on the principle that two hydrophobic surfaces bind to each other, when getting in physical contact. The Sorbact pad consists of two components. The first component has one or more liquid permeable layers of a hydrophobic, bacteria adsorbing, physiologically innocuous material containing a woven or nonwoven hydrophilic fabric. The fabric has been rendered hydrophobic by chemical treatment with a compound containing hydrophobic groups. The second component consists of one or more layers of a hydrophilic, liquid adsorbing, physiologically innocuous material. The hydrophilic liquid absorbing material effects a liquid flow by suction of exudate from the wound. If the microorganisms exhibit hydrophobic surface structures they will accompany this flow of liquid and come in contact with the hydrophobic component and bind.

Even if the traditional Sorbact pad product solves an important problem of reducing the number of microorganisms in a wound without using chemicals or antibiotics, it has several disadvantages when used as a wound dressing. Firstly, it will need to be attached to the wound surface with a bandage using such materials as a cotton gauze wrap, surgical tape and the like. This means that there are several steps and products involved for the user to apply the Sorbact pad, which among other things leads to increased costs and time to handle. Further, such a combined bandage will be sensitive to liquids, such as water, moisture, dirt, microorganisms etc. from the outside, being possible to penetrate the bandage. Further, it has been showed that a good contact between the wound and the hydrophobic fabric is important for an efficient attachment/binding of the unwanted microbes of the wound. Depending on the location on the body of the wound, this is not always easy to achieve with the loose pad and a bandage. Further, it is difficult to inspect the status of the wound in terms of inflammation etc. through a bandage.

Now, therefore the invention herein was made to address the above problems.

It is an object of the invention herein to provide a product ideal for the treatment of wounds and a method of making this product. It is a further object of the invention to provide a product that protects the wound, absorbs exudate and reduces the number of pathogenic microorganisms, without using antimicrobial substances. It is a further object of the invention to provide a product that may be made visually transparent, as well as being semi-permeable and self-adhesive, allowing passage of oxygen and moisture and inspection of the surrounding skin at the same times as the product binds existing pathogens and prevents the entry of new pathogens from the outside.

SUMMARY OF THE INVENTION

The invention herein relates to a wound dressing product, combining both a traditional dressing with a mounted absorbent material and a hydrophobic fabric attached thereto, which is to be placed towards the wound, and is capable of binding unwanted micro organisms. The product of the invention is ideal for treatment of wounds. It protects the wound, absorbs exudate and reduces the number of pathogenic microorganisms, without using antimicrobial substances. It consists basically of three bonded layers: hydrophobic cellulose acetate fabric which binds microorganisms, an attached efficient absorbent material, and a backing (cover) which in the preferred embodiment is visually transparent, semi-permeable and self-adhesive. These properties of the one-piece product of the invention allow passage of oxygen and moisture and inspection of the surrounding skin at the same times as the product binds existing pathogens and prevents the entry of new ones from the outside. The dressing is waterproof and allows the user to shower.

Other objects and features of the inventions will be more fully apparent from the following disclosure and appended claims.

BRIEF DESCRIPTION OF THE DRAWINGS

In FIG. 1a, the product is shown above a wound surface, on which there are bacteria schematically shown, before placement of the product on the wound. In FIG. 1b, the product is shown on the wound surface. In FIG. 1c, the product is shown upon removal from the wound.

FIG. 3 is a perspective view of a vein catheter bandage according to the invention herein.

FIG. 4 is a schematic cross-sectional view of the completely assembled invention in use.

DETAILED DESCRIPTION OF THE INVENTION AND PREFERRED EMBODIMENTS THEREOF

The product of the invention is ideal for treatment of wounds. It protects the wound, absorbs exudate and reduces the number of pathogenic microorganisms, without using antimicrobial substances. The product of the invention consists of three bonded layers: hydrophobic cellulose acetate fabric that binds microorganisms, an attached efficient absorbent material and a backing (cover) which is preferably visually transparent, semi-permeable and self-adhesive.

Figure 1A:
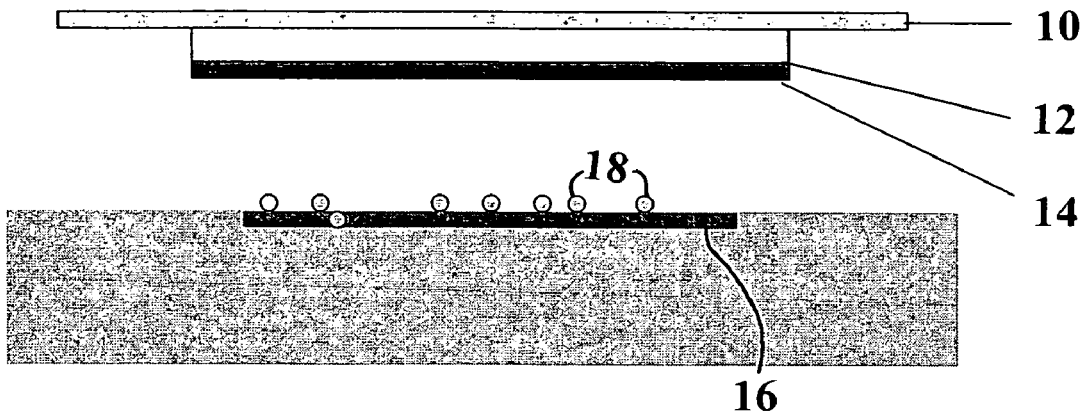
FIGS. 1a-1c are schematic drawings of a cross-sectional side view of the invention as it may be used.
Figure 1B:
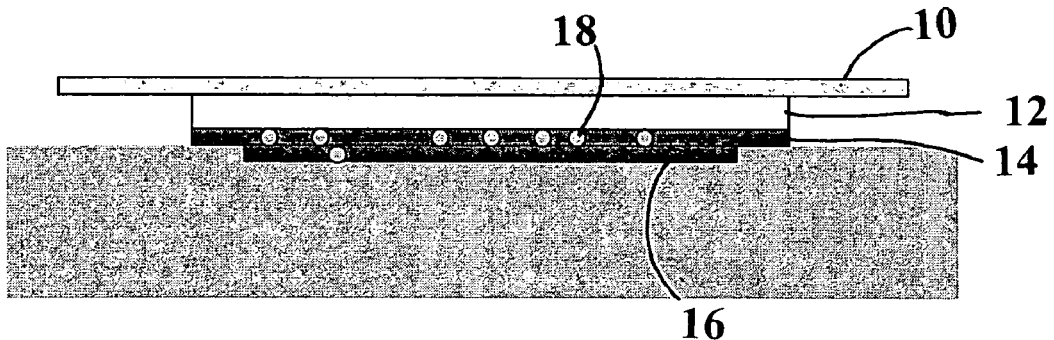
Figure 1C:
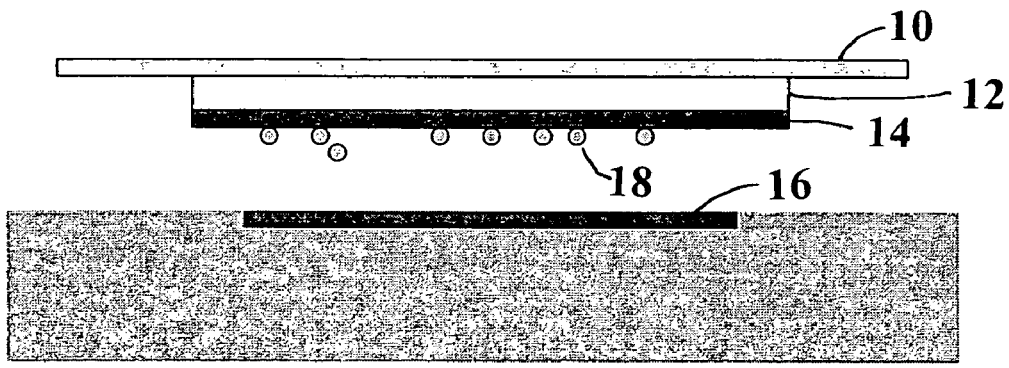

Referring now to the figures, FIGS. 1a-1c are a schematic representation of the use of the invention to bind microorganisms, showing the cover layer (carrier/backing) 10, absorbent layer 12 and hydrophobic layer 14 above a wound area 16 on which bacteria 18 are depicted, showing sequentially before, during and after application to a wound, respectively.

Figure 2:
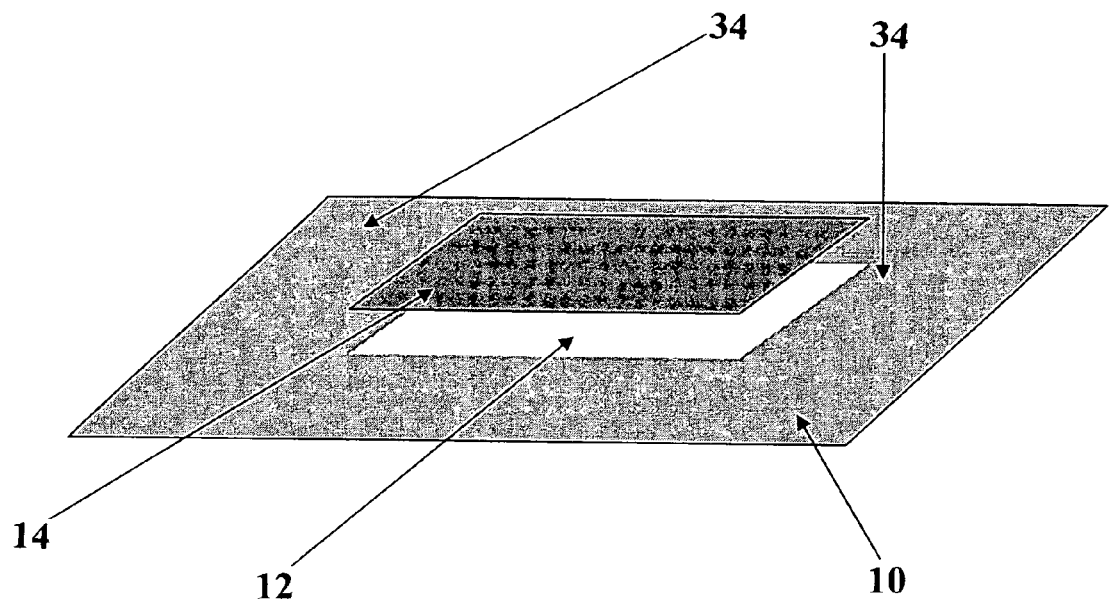
FIG. 2 is a perspective schematic drawing of the invention.

The product of the invention is shown schematically in perspective view in FIG. 2, and in cross-section in FIG. 4 (both figures have the cover shown on the bottom of the figure). In FIG. 4 is shown the hydrophobic layer 14, preferably made of cellulose acetate which has been made strongly hydrophobic with treatment of DACC. The hydrophobic layer 14 is in direct contact with the wound site 16. Adhesive layer 24 is preferably hot melt based on thermoplastic latex, and attaches the hydrophobic layer 14 to the absorbent core 12, which basically is made up of cellulose fibers with latex as a binding agent. Adhesive layer 22 attaches the absorbent core 12 to the visually transparent film carrier layer 10 (cover). A self-tacking adhesive 34 is designed to stick to the skin of the wearer of the wound dressing. Protection layer (release layer) 20 is preferably made of siliconized paper which is to be removed when the wound dressing is applied to the wound site.

These properties of the product allow passage of oxygen and moisture and makes inspection of the surrounding skin possible. The dressing is preferably waterproof and allows the user to shower. It is easy to use as all layers are bonded into a ready-to-use product, using a method that bonds the product well without disturbing the transfer of liquids between layers. The product of the invention reduces the risk of dirt, pathogens etc entering from the outside and gives an optimal contact between the hydrophobic material and the wound, improving the binding of unwanted microorganisms.

The product is manufactured in several steps and with several components. As one object of the invention is to have a "one-piece", reliable and easy to use product, a good bonding between the components is required. This requirement, especially in the case of bonding between the absorbent, hydrophilic, material and the hydrophobic fabric, is contradictory to other requirements of the product as a good absorber of wound exudates and it's permeability. This is due to the fact that the very hydrophobic fabric is difficult to bond well with the absorbent material without using adhesive in an amount or manner of use, or of a quality, that will hinder the transport of fluids through the first bacteria binding layer into the absorbent layer. It was necessary to solve this issue for the present invention so that the product structure could be developed, and materials and adhesive be selected for a good bonding of the hydrophobic material, without compromising transfer of fluids. Also, standard production equipment for bonding of fabrics etc needed to be rebuilt to incorporate a second heating step in the lamination of the two components.

The hydrophilic material used in the invention is preferably a material with very good absorption capacity and stability for it's size and weight. One such type of material is air laid cellulose for example Concert MH080.104.P000 (from Concert GmbH, in Falkenhagen, Germany) made of cellulose fibers with a synthetic binder (Ethylene Vinyl Acetate).

A requirement of the material in the absorption layer is to have an absorption capacity in the range of 3-60 g/g weight, preferably 5-35 g/g, measured according to ISO 111948-1, and to contain an amount and composition of a binding agent (s) that are compatible and supportive of the bonding to the hydrophobic material. Example of such binding agents is Ethylene Vinyl Acetate. Such binding agent should be more than 6% of the total weight of the hydrophilic material, and is preferably more than 12% by weight. Other examples of hydrophilic, liquid-absorbing physiologically innocuous materials with suitable binding agents are special tissue paper, cross-linked polysaccarides, vinyl polymers and acryl polymers. Examples of cross-linked polysaccharides are methyl cellulose, ethyl cellulose, hydroxyethyl cellulose, dextran or starch cross-linked with the aid of a bifunctional cross-linking agent such as a bifunctional glycerol derivative of the type dichlorohydrin or dibromohydrin or the corresponding epoxide compounds obtainable by splitting-off hydrogen halide, i.e. epichlorohydrin and epibromohydrin, or a diepoxide such as 1,2-3,4-diepoxybutane. Examples of other hydrophilic polymers are acryl polymers, which may be cross-linked linked with, for instance, methylenebisacrylamide.

The hydrophobic material may comprise, for example, a hydrophobic fabric or hydrophobic non-woven fabric, or a hydrophilic fabric or nonwoven fabric which has been rendered hydrophobic by a special treatment, or a hydrophobic, perforated foil. Hydrophobic woven and non-woven fabrics may be produced from synthetic fibers or the type polyamide, polypropylene and polytetrafluoroethylene fibers, or from carbon fibers. In order to obtain a hydrophobic material from a woven or non-woven hydrophilic fabric, such as woven or non-woven cotton fabric, the fabric may be treated chemically for example, in a known manner, with a compound containing hydrophobic groups, for example with a dialkyl-carbamoyl chloride such as dihexadecyl-carbamoyl chloride or dioctadecyl-carbamoyl chloride. A preferred hydrophobic layer of the invention is made of green cellulose acetate to which dioctadecyl carbamoyl chloride is applied as discussed in the examples.

The hydrophobic material is to be bonded to the hydrophilic material with the aid of a suitable adhesive, for example a hot-melt by the name of Dispomelnt 505E (National Starch & Chemical Ltd, Slough Berkshire, United Kingdom), which is based on Styrene Butadiene Styrene block polymers (SBS) or Dispomelt 250E, which is based on Amorfous Poly Alpha Styrene or hot melts based on Ethylene Vinyl Acetate. These hot melts are generally called thermoplastic latex. Other adhesives known in the art could also be used, but in order to get a sufficiently strong bond without blocking the transfer of fluids in the product, it is important to select an adhesive that functions well together with the binding agent of the hydrophilic agent. The adhesive component, such as hot-melt, is applied heated to either the hydrophobic or hydrophilic material by using a slot applier, spraying or roll coating, such as reverse roll, direct roll, 5-roll multi-roll, 3-roll offset, offset gravure, die, pressure, saturators, rod, and Meyer rod coating as a very thin layer at an amount of <10 $g/m^2$, preferably <8 $g/m^2$ and then laminated between two rollers for the final bonding. It is to be noted that the pressure rollers (nip rolls) for the bonding need to be equipped with an internal heating element, or the like, for a second heating step, after the application of the adhesive, with a temperature in the range of 120-150° C. and a compression rate between 20-75%, preferably 40-60%, in order to achieve a sufficiently strong bond to the hydrophobic material. The strength of the lamination, as determined in a wet-test as described in the example below, should be of at least 10 gram/cm, but preferably >20 gram/cm width.

Next, the backing (cover) of the product is attached. This is done after the two bonded materials are cut into suitable size pads. The backing is made of a suitable material which is semi-permeable, self-adhesive and preferably visually transparent. One such material is polyurethane film with a suitable adhesive known in the art for example DURO-TAK 380-2954 (National Starch & Chemical Ltd, Slough Berkshire, United Kingdom).

The film should have a water vapor permeability of preferably 100-1000 g moisture/$m^2$/24 h at 38° C., but not more than 2000 g/$m^2$/24 h at 38° C. These properties of the product allow passage of oxygen and of moisture and in the case of a transparent film, inspection of the surrounding skin.

The microorganisms will be removed from the wound when the dressing is changed. Hence, the number of microorganisms decreases over time to a number which the body can control and the wound can heal. Since microbes adhere to the dressing by hydrophobic interactions, spread of microorganisms to the environment during changing of dressings is limited. The combined bacteria-binding capacity and absorption of wound secretion, pus and debris provide optimal cleansing of the wound. With this method, the bacterial load in the wound surface is reduced rapidly and effectively. The body's own defense mechanism can then take over, and the natural healing process can continue. The use of a hydrophobic layer, even without systemic antibiotic therapy, decreases the number of infecting microorganisms but does not eliminate all bacteria which is an advantage since a small number of microorganisms stimulate wound healing. The invention replaces the use of topical antibiotics, and hence reduces the spread of antibiotic resistant organisms.

To the extent that there is a reduced risk of sores drying out, which can have an inhibiting effect on the healing process, the absorption capacity of the hydrophilic layer can be altered in various versions of the product, as well as regulated by the permeability of the polyurethane cover.

Other objects and features of the inventions will be more fully apparent from the following examples and appended claims.

EXAMPLE 1

Manufacture of Wound Dressing Product

In this example we manufacture a standard wound dressing based on the invention in the following manner:

Materials: (from inside-out see FIG. 4)

| | LAYER | COMMERCIAL PRODUCT NAME | MANUFACTURER |
|---|---|---|---|
| 1. | Hydrophobic layer | Green Cellulose Acetate woven prepared according to U.S. Pat. No. 4,617,326 | ABIGO Medical AB Sweden |
| 2. | Adhesive | National 505E | National Starch & Chemical Ltd., United Kingdom |
| 3. | Absorbent material | (Airlaid) Concert MH080.104.P000 | Concert GmbH, Falkenhagen, Germany |
| 4. | Adhesive | National 505E | National Starch & Chemical Ltd., United Kingdom |
| 5. | Carrier layer | Polyurethanefilm, 3M, 9482 no. ID 70-0000-6538-6 | 3M, St Paul, MN, U.S.A. |
| 6. | Adhesive: | DURO-TAK 380-295 | National Starch & Chemical Ltd., United Kingdom |
| 7. | Siliconized release paper, | Loparex ESP35TEE | Loparex OY Lohja, Finland |

A. The hydrophobic layer is preferably produced according to U.S. Pat. No. 4,617,326 by applying to a cellulose acetate fabric an amount of dioctadecyl carbamoyl chloride as disclosed in this patent making a covalent bond between the materials. The acetate fabric is on rolls of 50 m length and at a width of 1 m, and taken as such to the next step.

B. The bonding of the hydrophobic layer with the absorbent layer is made in a machine for the purpose, having a suitable applicator for the hot-melt, a slot applier, and heated rolls for the bonding of the two materials, so called nip rolls, as is known in the art. In order to minimize the risk for the adhesive to bleed through the surface layer it is preferable to put the hot melt layer on the air laid. In prior test runs it was found that the risk for the adhesive to bleed through the hydrophobic cellulose acetate layer increases dramatically if the amount of adhesive is >10 g/m$^2$. Decreasing the amount of adhesive, however, reduces the lamination strength. The ideal amount of adhesive is between 7-10 g/m$^2$. In our prior test runs we found a hot melt temperature of 150 degrees C. to work well together with pre heated nip rolls.

Test of Lamination Strength:

The test sample is placed in water solution with 0.9% NaCl or defibrillated sheep blood for one hour. The layers are separated from each other and the lamination strength is measured. If possible it should be at least 10 gram/cm, but preferably >20 gram/cm width Because it can sometimes be difficult to get hold of the layers in order to separate them, a knife or tweezers with sharp edges may be used, or the sample may be prepared prior to the water test by separating the layers from each other by leaving flaps to grab.

Other Tests:

Adhesive bleeding through the green cellulose acetate woven fabric is tested by pressing samples of the laminated material surface layer (green woven material) hard against each other. Only a minor sticking is acceptable.

Blood clotting is tested by application of 0.3 ml of defibrillated sheep blood on top of the lamination. The blood should easily pass through the green cellulose acetate woven layer and leave only small amounts of blood on the surface.

After the bonding process of the hydrophobic acetate layer and the absorbing layer, the now bonded materials are still in a roll form, which is taken to the cutting step.

C. Cutting and Adding of Carrier Layer.

The now bonded hydrophobic layer and absorbing layer is cut into suitable size pieces for the final product, in this case 30 mm×30 mm. The cut pieces are placed on carrier-film, prepared with the adhesive and release paper (see FIG. 4), and in strips of 100 mm. The bonded pieces are centered on the carrier strips and with a distance from center to center of 80 mm. A release paper of the same with is finally then applied on inner side. The now completely assembled dressing, is cut into pieces of 100 mm×80 mm, sterilized and then packed 10 by 10 in cartons.

EXAMPLE 2

Use of the New Dressing Product to Bind Pathogens

Material: Wound dressing as described in Example 1
Bacterial strains: *Staphylococcus aureus* Newman, *Pseudomonas aeruginosa* 510, *Enterococcus faecalis*, *Candida albicans*

Isolates were cultured on agar with 5% horse erythrocytes in 5% $CO_2$ atmosphere at 37° C. Suspensions were made in phosphate-buffered saline (PBS, 0.02 M sodium phosphate and 0.15 M sodium chloride, pH 7.2) at $10^9$ bacterial cells/ml, $10^7$ fungal cells/ml or indicated concentration.

The dressing was cut in 1 cm$^2$ pieces. Incubation was made in 24 well polymer plates. 1 ml of suspension was added to each dressing. The plates were placed on a rotary shaker at very low speed. Incubation was performed at room temperature for the indicated time. After incubation, dressings were rinsed in PBS several times, and then put in 2.5% TCA (tricarboxylic acid).

The ATP content was measured in a luminometer (LKB Wallac). Controls: Number of adhered bacteria (CFU/ATP) were normalized against total added bacteria (CFU/ATP), and blank (no bacteria, only EDTA-Tris buffer) was the ATP value control. (FIG. 11).

Figure 5:
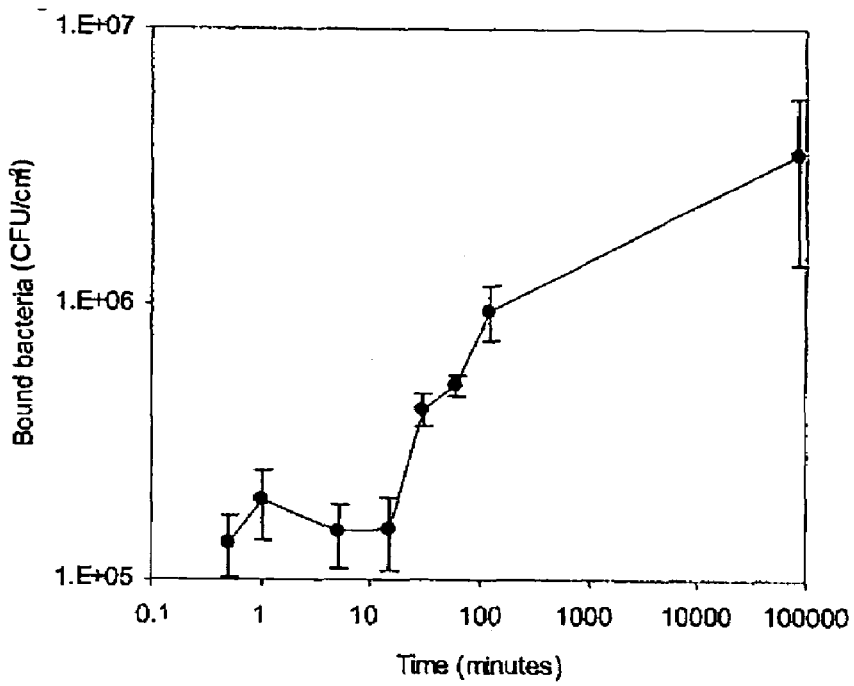
FIG. 5 is a graph of binding of *Staphylococcus aureus* ($CFU/cm^2$) to a test dressing of the invention, as a function of time.

Results: (FIG. 5-10)
*S. aureus* >$10^5$ cells adhered during 30 sec, 1, 5 and 10 minutes, and then increased to $10^6$ cells after 2 hrs. Some multiplication occurred during the following 24 hrs to reach 5×$10^6$ cells/cm$^2$ (FIG. 5).

Figure 6:
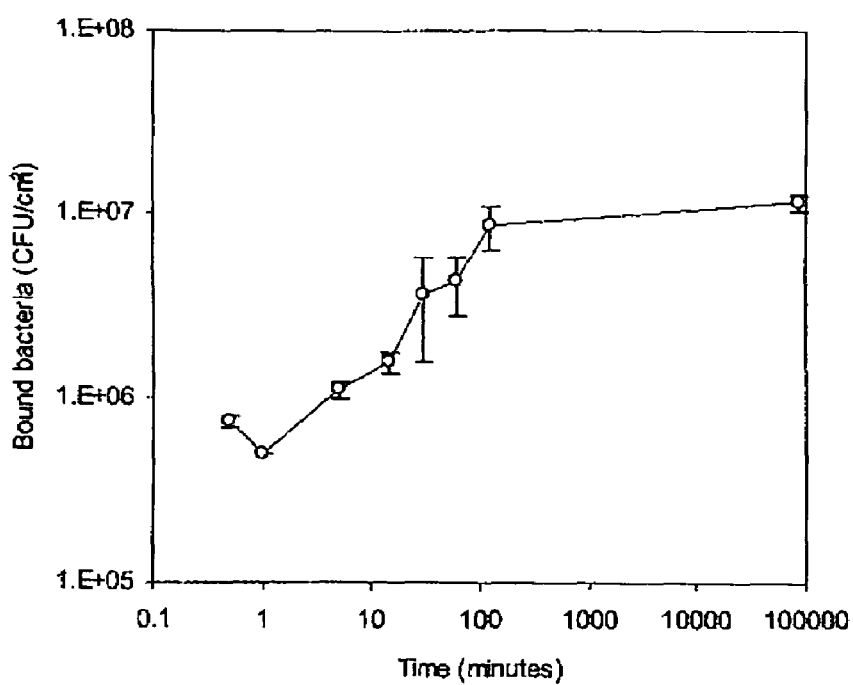
FIG. 6 is a graph of binding of *Pseudomonas aeruginosa* ($CFU/cm^2$) to a test dressing of the invention, as a function of time.
Figure 7:
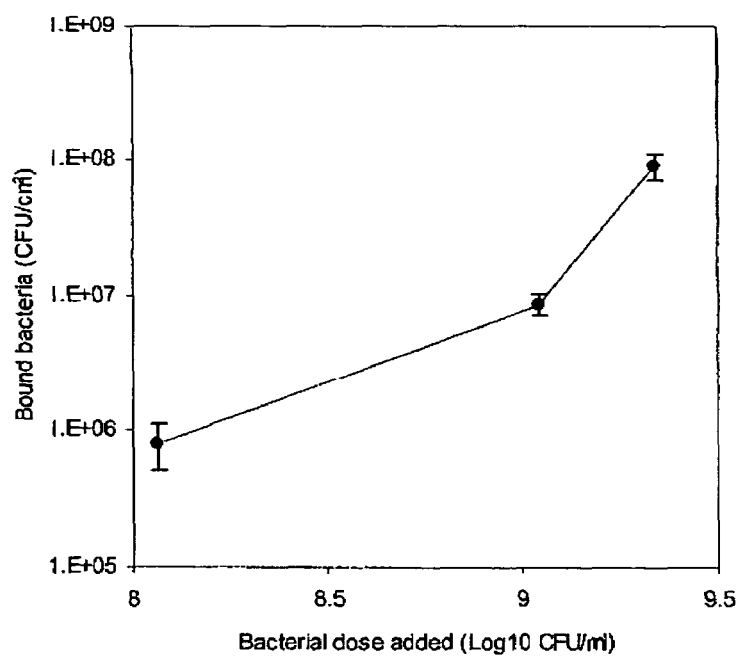
FIG. 7 is a graph of binding of *Staphylococcus aureus* ($CFU/cm^2$) to a test dressing of the invention, as function of bacterial dose added ($Log_{10}$ CFU/ml).
Figure 8:
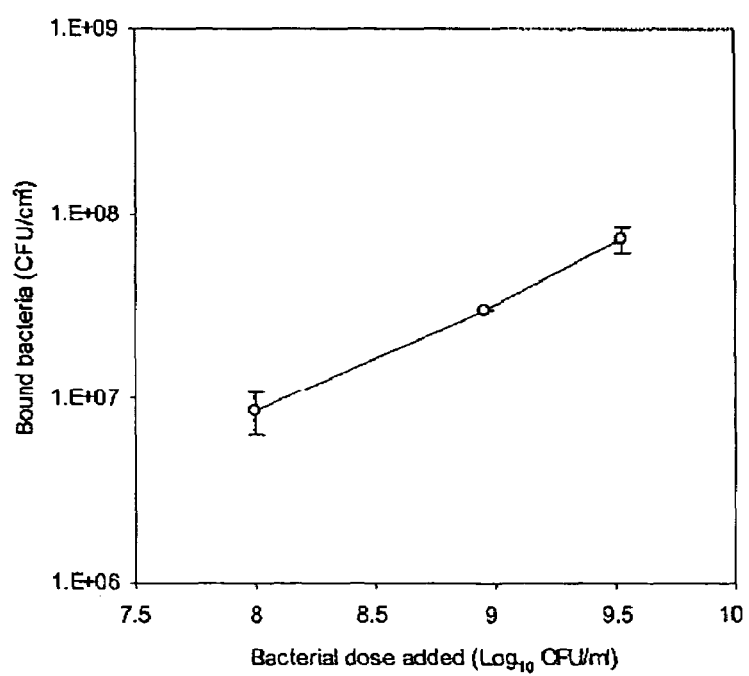
FIG. 8 is a graph of binding of *Pseudomonas aeruginosa* ($CFU/cm^2$) to a test dressing of the invention, as function of bacterial dose added ($Log_{10}$ CFU/ml).
Figure 9:
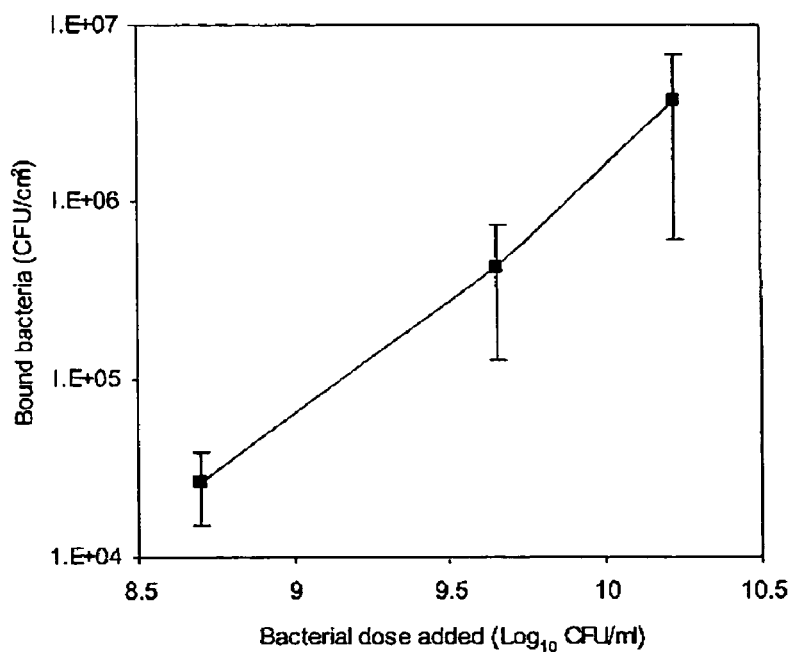
FIG. 9 is a graph of binding of *Enterococcus* ($CFU/cm^2$) to a test dressing of the invention, as function of bacterial dose added ($Log_{10}$ CFU/ml).
Figure 10:
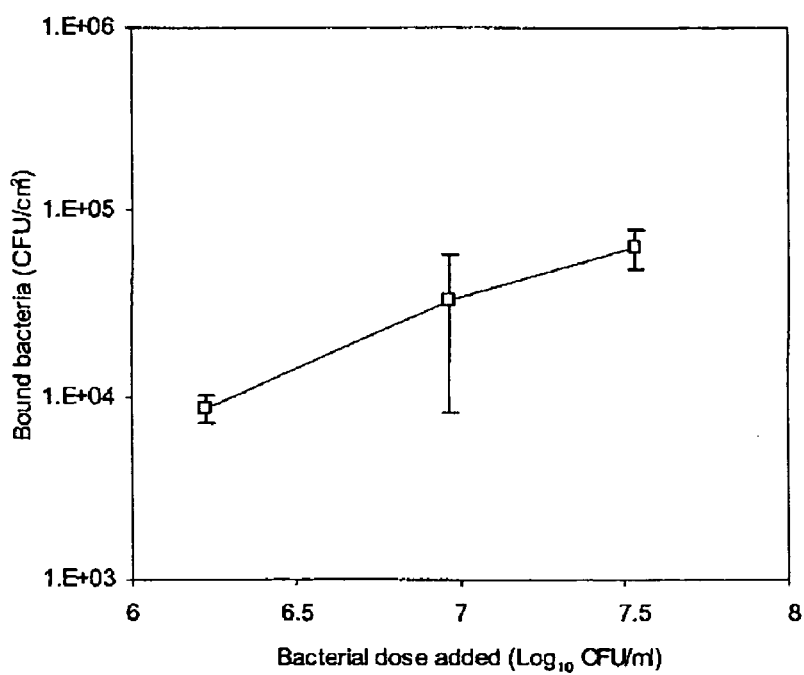
FIG. 10 is a graph of binding of *Candida albicans* ($CFU/cm^2$) to a test dressing of the invention, as function of bacterial dose added ($Log_{10}$ CFU/ml).

*P. aeruginosa* Around $10^6$ cells adhered during 30s, 1, 5 and 10 min, and then increased during 30 and 60 min incubation to reach $10^7$ cells/cm$^2$ after 2 hrs incubation. No multiplication of adhered bacteria occurred during the following 24 hrs (FIG. 6).

We did not reach endpoints for maximal adsorption. When $5\times10^9$ cells of *S. aureus* were added, $10^8$ cells adhered, for *P. aeruginosa* $10^8$ cells adhered out of $10^{9.5}$ added, and for *E. faecalis* $8\times10^6$ out of $5\times10^{10}$ added. For *C. albicans* the slope levels off, $10^5$ cells adhered out of $10^{7.5}$ added (FIG. 11).

Conclusion: The test dressing with the hydrophobic layer is a good adsorber of different important and potential pathogens in wound healing.

EXAMPLE 3

Manufacture of a Vein Catheter Dressing

In this example, a vein catheter dressing based on the invention was manufactured. The manufacture is made according to Example 1 for the first steps and then with a revised Step C as follows:

C. Cutting and Adding of Carrier Layer.

The now bonded hydrophobic layer and absorbing layer is cut into suitable pieces for a vein catheter product, in this case 20 mm×20 mm. The cut pieces are placed on carrier-film, prepared with the adhesive and two release papers 20 with folded gripping tabs 28 (see FIG. 3), and in strips of 100 mm. The bonded pieces are centered on the carrier strips and with a distance from center to center of 100 mm. A release paper of the same width is then applied on inner side. The now completely assembled dressing, is cut into pieces of 100 mm× 60 mm, cutting 20 mm from the pad of attached layers in the top end and cutting a slit for the catheter from the opposite side to a distance close to the pad preferably 5 mm before the pad. In another embodiment the cutting slit can enter into the pad preferably no more than half of the width of the pad. FIG. 3 also shows a cutaway area 30 for purposes of viewing the layers, and the catheter slit 32. The product is finally sterilized and then packed 10 by 10 in cartons.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A dressing for a wound, comprising:
    a) a hydrophobic liquid permeable layer capable of binding microorganisms, wherein the hydrophobic layer is hydrophobic due to chemical treatment with a compound containing hydrophobic groups;
    b) an absorbent hydrophilic layer; and
    c) a cover layer, wherein the hydrophobic layer is adhesively attached to the absorbent hydrophilic layer by a thin layer of less than 10 g/m$^2$ of a hot-melt adhesive, and the absorbent hydrophilic layer is positioned between the hydrophobic layer and the cover layer,
    wherein when the dressing is positioned on the wound, fluids pass through the hydrophobic layer into the absorbent hydrophilic layer.

2. The dressing for a wound according to claim 1, wherein the compound is dioctadecyl carbamoyl chloride.

3. The dressing for a wound according to claim 1, wherein the absorbent hydrophilic layer comprises a cellulose air-laid material and binders of latex.

4. The dressing for a wound according to claim 1, wherein the absorbent hydrophilic layer has an absorption capacity of 3-60 g/g.

5. The dressing for a wound according to claim 1, wherein the absorbent hydrophilic layer is treated with a binding agent to optimize bonding to the hydrophobic layer.

6. The dressing for a wound according to claim 1, wherein the cover layer is made of polyurethane film.

7. The dressing for a wound according to claim 1, wherein the cover layer is visually transparent.

8. The dressing for a wound according to claim 1, wherein the cover layer is self-adhesive.

9. The dressing for a wound according to claim 1, wherein the cover layer is semi-permeable.

10. The dressing for a wound according to claim 9, wherein the cover layer has a permeability of 100-1000 g moisture/m$^2$/24 hours at 38° C.

11. The dressing for a wound according to claim 1, wherein the cover layer is semi-permeable, self-adhesive, and visually transparent.

12. The dressing for a wound according to claim 1, wherein the dressing has a lamination strength in wet stage of at least 10 g/cm width.

13. The dressing for a wound according to claim 1, wherein the dressing is a vein catheter dressing.

14. The dressing for a wound according to claim 1, wherein the hydrophobic layer is hydrophobic due to dioctadecyl carbamoyl chloride being coupled to the layer.

15. The dressing for a wound according to claim 1, further comprising a binding agent that is more that 6% by weight of the hydrophilic layer.

16. A method of preparing a wound dressing, comprising adhesively attaching a liquid permeable hydrophobic layer capable of binding microorganisms to an absorbent hydrophilic layer using a thin layer of less than 10 g/m$^2$ of a hot-melt adhesive; and adhesively attaching a cover layer, wherein the absorbent hydrophilic layer is positioned between the liquid permeable hydrophobic layer and the cover layer, wherein when the wound dressing is positioned on the wound, fluids pass through the hydrophobic layer into the absorbent hydrophilic layer.

\* \* \* \* \*